(12) United States Patent
Choi et al.

(10) Patent No.: US 11,759,490 B2
(45) Date of Patent: Sep. 19, 2023

(54) PROCESS FOR PRODUCTION OF RED GINSENG HYDROLYSIS CONCENTRATE HAVING ENRICHED SPECIFIC COMPONENT

(71) Applicant: DAEDONG KOREA GINSENG CO., LTD, Chungcheongnam-do (KR)

(72) Inventors: Sung-Keun Choi, Chungcheongnam-do (KR); Chang-Soon Lee, Chungcheongbuk-do (KR); Sung Soo Jang, Chungcheongnam-do (KR); Byeong-Seon Jeon, Daejeon (KR); Kun Hee Lee, Daejeon (KR); Hye Jeong Jeon, Daejeon (KR); Da Young Kim, Daejeon (KR); Hye Won Kim, Daejeon (KR); Han-Min Kim, Chungcheongnam-do (KR); Byoung Man Kong, Gyeonggi-do (KR)

(73) Assignee: DAEDONG KOREA GINSENG CO., LTD, Chungcheongnam-Do (KR)

( * ) Notice: Subject to any disclaimer, the term of this patent is extended or adjusted under 35 U.S.C. 154(b) by 11 days.

(21) Appl. No.: 17/693,913

(22) Filed: Mar. 14, 2022

(65) Prior Publication Data
US 2022/0378862 A1    Dec. 1, 2022

(30) Foreign Application Priority Data

May 26, 2021  (KR) .................. 10-2021-0067696

(51) Int. Cl.
| | | |
|---|---|---|
| *A61K 36/258* | (2006.01) | |
| *A23L 5/20* | (2016.01) | |
| *A23L 33/105* | (2016.01) | |
| *A61K 36/03* | (2006.01) | |
| *A61K 36/14* | (2006.01) | |
| *A61K 36/28* | (2006.01) | |
| *A61K 36/899* | (2006.01) | |
| *B01D 11/02* | (2006.01) | |

(52) U.S. Cl.
CPC .............. *A61K 36/258* (2013.01); *A23L 5/23* (2016.08); *A23L 33/105* (2016.08); *A61K 36/03* (2013.01); *A61K 36/14* (2013.01); *A61K 36/28* (2013.01); *A61K 36/899* (2013.01); *B01D 11/0288* (2013.01); *A23V 2002/00* (2013.01); *A61K 2236/331* (2013.01); *A61K 2236/333* (2013.01); *A61K 2236/37* (2013.01); *A61K 2236/53* (2013.01)

(58) Field of Classification Search
None
See application file for complete search history.

(56) References Cited

FOREIGN PATENT DOCUMENTS

| | | |
|---|---|---|
| KR | 10-0377546 B1 | 3/2003 |
| KR | 10-2016-0047987 A | 5/2016 |
| KR | 10-1822024 B1 | 1/2018 |
| KR | 10-2020-0136648 A | 12/2020 |
| KR | 10-2258796 B1 | 6/2021 |
| WO | WO 2011/059212 A2 | 5/2011 |

OTHER PUBLICATIONS

European Search Report For EP 22159103.5 dated Sep. 13, 2022 from European patent office in a counterpart European patent application.
Park, Yeong-Ju et al., "Optimal bioconversion for compound K production from red ginseng root (C.A. Mayer) by sequential enzymatic hydrolysis and its characteristics ", Applied Biological Chemistry, vol. 64, No. 1, Jan. 25, 2021, XP037348810, ISSN: 2468-0834, DOI: 10.1186/S13765-020-00587-X.

*Primary Examiner* — Susan Hoffman
(74) *Attorney, Agent, or Firm* — The PL Law Group, PLLC

(57) ABSTRACT

A method for production of red ginseng hydrolysis concentrate according to an embodiment of the present disclosure includes carrying out an enzyme reaction of red ginseng concentrate by adding an enzyme solution followed by addition of alcohol to prepare a mixture solution of red ginseng and alcohol, and centrifuging the prepared mixture solution of red ginseng and alcohol followed by concentration under reduced pressure of a supernatant separated by the centrifuge, and a red ginseng hydrolysis concentrate produced by the aforementioned process.

6 Claims, No Drawings

PROCESS FOR PRODUCTION OF RED GINSENG HYDROLYSIS CONCENTRATE HAVING ENRICHED SPECIFIC COMPONENT

CROSS-REFERENCE TO RELATED APPLICATION(S)

This application claims the benefit under 35 USC §119(a) of Korean Patent Application No. 10-2021-0067696, filed on May 26, 2021, in the Korean Intellectual Property Office, the entire disclosure of which is incorporated herein by reference for all purposes.

BACKGROUND

1. Technical Field

The present invention relates to a process for production of red ginseng hydrolysis concentrate comprising: carrying out an enzyme reaction of red ginseng concentrate by adding an enzyme solution followed by addition of alcohol to prepare a mixture solution of red ginseng and alcohol; and centrifuging the prepared mixture solution of red ginseng and alcohol followed by concentration under reduced pressure of a supernatant separated by the centrifuge, and a red ginseng hydrolysis concentrate produced by the aforementioned process. According to the present invention, red ginseng hydrolysis concentrate containing a large amount of compound K can be provided without compromising the product quality of the red ginseng concentrate.

2. Background Art

Panax as a common name of Korean ginseng is a compound word of two Greek words, Pan (all) and Axos (cure), meaning "cure for all disorders", and it is a medicinal plant which has been most widely consumed as general food and medicine. Ginseng is composed of carbohydrates (about 60%), crude proteins (8 to 15%), crude lipids (1 to 3%), ash (4 to 6%), crude saponin (3 to 7%), and other minor components. Ginseng is known to have functional benefits like immunity enhancement, fatigue recovery, memory improvement, blood circulation improvement, anti-oxidation, and health maintenance in menopausal women. It is also reported that ginseng has various pharmacological activities like suppressing or stimulating central nervous system, promoting biosynthesis of proteins and nucleic acids, promoting hematopoiesis, preventing arteriosclerosis, lowering blood glucose level, and anti-stress activity. It is known that those activities are mainly based on the effect of ginsenosides, which are generated from saponin upon release of sugars.

More than 30 kinds of ginsenosides have been separated and identified from ginseng saponin, and ginsenosides Rb1, Rb2, Rc, and Rd, which belong to protopanaxadiol-based saponin, and ginsenosides Re and Rg1, which belong to protopanaxatriol-based saponin, are the major components.

It is known that ginsenoside compound K (20-O-beta-D-glucopyranosyl-20(S)-protopanaxadiol) as a metabolite of ginsenoside has a high pharmacological activity as well as excellent absorption property in human body. In recent years, it is also reported to exhibit a therapeutic effect for macular degeneration and neuropathic pain. In addition, it is currently known to exhibit various favorable effects like inhibition of tumor angiogenesis, inhibition of cancer cell infiltration, inhibition of cancer cell proliferation, and immunity enhancement.

However, since ginsenoside compound K is hardly contained in ginseng itself, a technique for converting ginsenosides contained in ginseng to compound K by using enzyme or radiation has been developed to solve the problem. Still, development of a new method for producing enriched ginsenoside compound K is in need.

In Korean Patent Registration No. 0377546, a method of producing ginsenoside compound K based on enzymatic process is disclosed, and in Korean Patent Publication No. 2020-0136648, a method for production of a composition for preparing ginsenoside compound K using *Aspergillus oryzae* enzyme solution is disclosed. However, those methods are different from the process of the present invention which is aimed to produce red ginseng hydrolysis concentrate having enriched specific component

SUMMARY

The present invention is devised under the circumstances that are described in the above. To enhance the content of compound K in red ginseng concentrate, production conditions such as selection of submaterials, pretreatment process of red ginseng, production of concentrate, and the like are optimized so that a process for producing red ginseng hydrolysis concentrate with high quality and containing a large amount of compound K is provided.

To achieve the object described in the above, the present invention provides a process for production of red ginseng hydrolysis concentrate comprising: (1) adding water or alcohol to a mixture containing bamboo shoot, Japanese gerbera (*Leibnitzia anandria*) leaf, oriental arbor vitae (*Platycladus orientalis*) fruit, and false daisy (*Eclipta prostrata*) followed by extraction and filtration to prepare an extract; (2) adding water or alcohol to *Ecklonia cava* followed by extraction to prepare an *Ecklonia cava* extract; (3) adding the extract prepared in the above step (1) to red ginseng followed by extraction and filtration to prepare a red ginseng extract; (4) adding the *Ecklonia cava* extract prepared in the above step (2) to red ginseng separated from the red ginseng extract prepared in the above step (3) followed by extraction and filtration to prepare a red ginseng extract; (5) mixing the red ginseng extract prepared in the above step (3) with the red ginseng extract prepared in the above step (4) followed by concentration to prepare red ginseng concentrate; (6) adding an enzyme solution to the red ginseng concentrate prepared in the above step (5) to have an enzyme reaction followed by addition of alcohol to prepare a mixture solution of red ginseng and alcohol; and (7) centrifuging the mixture solution of red ginseng and alcohol prepared in the above step (6) followed by concentration under reduced pressure of a supernatant separated by the centrifuge.

The present invention also provides a red ginseng hydrolysis concentrate produced by the aforementioned process.

According to the present invention, ginsenoside loss is minimized during the concentrate separation after the enzyme reaction and efficient conversion to compound K having excellent pharmacological effect is achieved so that red ginseng concentrate containing compound K at high concentration can be provided. In addition, due to the smooth taste obtained after the removal of bitterness, which is specific to red ginseng, easily swallowable red ginseng concentrate can be provided.

DETAILED DESCRIPTION

To achieve the object of the present invention, the present invention provides a process for production of red ginseng hydrolysis concentrate comprising:

(1) adding water or alcohol to a mixture containing bamboo shoot, Japanese gerbera (*Leibnitzia anandria*) leaf, oriental arbor vitae (*Platycladus orientalis*) fruit, and false daisy (*Eclipta prostrata*) followed by extraction and filtration to prepare an extract;

(2) adding water or alcohol to *Ecklonia cava* followed by extraction to prepare an *Ecklonia cava* extract;

(3) adding the extract prepared in the above step (1) to red ginseng followed by extraction and filtration to prepare a red ginseng extract;

(4) adding the *Ecklonia cava* extract prepared in the above step (2) to red ginseng separated from the red ginseng extract prepared in the above step (3) followed by extraction and filtration to prepare a red ginseng extract;

(5) mixing the red ginseng extract prepared in the above step (3) with the red ginseng extract prepared in the above step (4) followed by concentration to prepare red ginseng concentrate;

(6) adding an enzyme solution to the red ginseng concentrate prepared in the above step (5) to have an enzyme reaction followed by addition of alcohol to prepare a mixture solution of red ginseng and alcohol; and (7) centrifuging the mixture solution of red ginseng and alcohol prepared in the above step (6) followed by concentration under reduced pressure of a supernatant separated by the centrifuge.

According to the process for production of red ginseng hydrolysis concentrate of the present invention, the extract of the above step (1) may be preferably prepared by adding water or alcohol to a mixture containing, based on the total weight of the mixture, bamboo shoot at 36 to 40% by weight, Japanese gerbera (*Leibnitzia anandria*) leaf at 14 to 18% by weight, oriental arbor vitae (*Platycladus orientalis*) fruit at 28 to 32% by weight, and false daisy (*Eclipta prostrata*) at 14 to 18% by weight in a ratio of 7 to 9 (v/w) with respect to the mixture, extracting the resulting mixture for 6 to 10 hours at 90° C. to 100° C., and filtering the resulting mixture. More preferably, the extract may be prepared by adding water or alcohol to a mixture containing, based on the total weight of the mixture, bamboo shoot at 38% by weight, Japanese gerbera (*Leibnitzia anandria*) leaf at 16% by weight, oriental arbor vitae (*Platycladus orientalis*) fruit at 30% by weight, and false daisy (*Eclipta prostrata*) at 16% by weight in a ratio of 8 (v/w) with respect to the mixture, extracting the resulting mixture for 8 hours at 95° C., and filtering the resulting mixture.

Moreover, according to the process for production of red ginseng hydrolysis concentrate of the present invention, the *Ecklonia cava* extract of the above step (2) may be preferably prepared by adding water or alcohol to *Ecklonia cava* in a ratio of 7 to 9 (v/w) with respect to *Ecklonia cava*, and extracting the mixture for 7 to 9 hours at 90° C. to 100° C. More preferably, it may be prepared by adding water or alcohol to *Ecklonia cava* in a ratio of 8 (v/w) with respect to *Ecklonia cava*, and extracting the mixture for 8 hours at 95° C.

Moreover, according to the process for production of red ginseng hydrolysis concentrate of the present invention, the red ginseng extract of the above step (3) may be prepared by adding the extract to red ginseng, extracting the mixture at 80° C. to 90° C., and filtering the resulting mixture. More preferably, it may be prepared by adding the extract to red ginseng, extracting the mixture at 85° C., and filtering the resulting mixture.

Moreover, according to the process for production of red ginseng hydrolysis concentrate of the present invention, the red ginseng extract of the above step (4) may be preferably prepared by adding *Ecklonia cava* extract to red ginseng separated from the red ginseng extract, extracting the mixture at 80° C. to 90° C., and filtering the resulting mixture. More preferably, it may be prepared by adding *Ecklonia cava* extract to red ginseng separated from the red ginseng extract, extracting the mixture at 85° C., and filtering the resulting mixture.

By producing red ginseng concentrate at the conditions of above step (1) to step (4), smooth and rich taste can be enhanced while the bitterness specific to red ginseng is reduced so that red ginseng concentrate in which compound K is efficiently converted by the enzyme reaction can be provided.

Moreover, according to the process for production of red ginseng hydrolysis concentrate of the present invention, the mixture solution of red ginseng and alcohol of the above step (6) may be preferably prepared by adding an enzyme solution to the red ginseng concentrate, carrying out an enzyme reaction for 3 to 6 days at 45° C. to 65° C., and adding 65 to 95% (v/v) alcohol. More preferably, it may be prepared by adding an enzyme solution to the red ginseng concentrate, carrying out an enzyme reaction for 4 days at 50° C., and adding 70 to 80% (v/v) alcohol.

When the red ginseng concentrate is subjected to an enzyme reaction at the aforementioned conditions, ginsenosides contained in the red ginseng concentrate can be converted to compound K at high concentration. Meanwhile, as the enzyme may remain in the red ginseng concentrate after the completion of the enzyme reaction, lower quality of the enzyme concentration may be caused. Thus, it is preferable to remove the enzyme. Accordingly, by effectively removing the enzyme from the concentrate by centrifuge after adding alcohol, loss of the ginsenosides can be minimized.

As for the enzyme used for the aforementioned enzyme solution, at least one enzyme selected from a group consisting of carbohydrase such as viscozyme, promozyme, cellulaclast, termamyl, AMG, dextrozyme, BAN, novamyl, sumizyme L, sumizyme AC, or sumizyme TP5, proteinase such as flavourzyme, protamex, alcalase, neutrase, pepsin, collupulin MG, or sumizyme LP, pectinase such as pectinex, and a cellulose hydrolase such as plantase C150P or pluszyme may be used, but it is not limited thereto.

More specifically, the process for production of red ginseng hydrolysis concentrate of the present invention may comprise:

(1) adding water or alcohol to a mixture containing, based on the total weight of the mixture, bamboo shoot at 36 to 40% by weight, Japanese gerbera (*Leibnitzia anandria*) leaf at 14 to 18% by weight, oriental arbor vitae (*Platycladus orientalis*) fruit at 28 to 32% by weight, and false daisy (*Eclipta prostrata*) at 14 to 18% by weight in a ratio of 7 to 9 (v/w) with respect to the mixture followed by extraction for 6 to 10 hours at 90° C. to 100° C. and filtration to prepare an extract;

(2) adding water or alcohol to *Ecklonia cava* in a ratio of 7 to 9 (v/w) with respect to *Ecklonia cava* followed by extraction for 7 to 9 hours at 90° C. to 100° C. to prepare an *Ecklonia cava* extract;

(3) adding the extract prepared in the above step (1) to red ginseng followed by extraction at 80° C. to 90° C. and filtration to prepare a red ginseng extract;

(4) adding the *Ecklonia cava* extract prepared in the above step (2) to red ginseng separated from the red ginseng extract prepared in the above step (3) followed by extraction at 80° C. to 90° C. and filtration to prepare a red ginseng extract;

(5) mixing the red ginseng extract prepared in the above step (3) with the red ginseng extract prepared in the above step (4) followed by concentration to prepare red ginseng concentrate;

(6) adding an enzyme solution to the red ginseng concentrate prepared in the above step (5) to have an enzyme reaction for 3 to 6 days at 45° C. to 65° C. followed by addition of 65 to 95% (v/v) alcohol to prepare a mixture solution of red ginseng and alcohol; and (7) centrifuging the mixture solution of red ginseng and alcohol prepared in the above step (6) followed by concentration under reduced pressure of a supernatant separated by the centrifuge.

Even more specifically, the process for production of red ginseng hydrolysis concentrate of the present invention may comprise:

(1) adding water or alcohol to a mixture containing, based on the total weight of the mixture, bamboo shoot at 38% by weight, Japanese gerbera (*Leibnitzia anandria*) leaf at 16% by weight, oriental arbor vitae (*Platycladus orientalis*) fruit at 30% by weight, and false daisy (*Eclipta prostrata*) at 16% by weight in a ratio of 8 (v/w) with respect to the mixture followed by extraction for 8 hours at 95° C. and filtration to prepare an extract;

(2) adding water or alcohol to *Ecklonia cava* in a ratio of 8 (v/w) with respect to *Ecklonia cava* followed by extraction for 8 hours at 95° C. to prepare an *Ecklonia cava* extract;

(3) adding the extract prepared in the above step (1) to red ginseng followed by extraction at 85° C. and filtration to prepare a red ginseng extract;

(4) adding the *Ecklonia cava* extract prepared in the above step (2) to red ginseng separated from the red ginseng extract prepared in the above step (3) followed by extraction at 85° C. and filtration to prepare a red ginseng extract;

(5) mixing the red ginseng extract prepared in the above step (3) with the red ginseng extract prepared in the above step (4) followed by concentration to prepare red ginseng concentrate;

(6) adding an enzyme solution to the red ginseng concentrate prepared in the above step (5) to have an enzyme reaction for 4 days at 50° C. followed by addition of 70 to 80% (v/v) alcohol to prepare a mixture solution of red ginseng and alcohol; and (7) centrifuging the mixture solution of red ginseng and alcohol prepared in the above step (6) followed by concentration under reduced pressure of a supernatant separated by the centrifuge.

The present invention also provides red ginseng hydrolysis concentrate produced by the aforementioned process.

Hereinbelow, the present invention is explained in greater detail in view of the Examples. However, the following Examples are given only for exemplification of the present invention and it is evident that the scope of the present invention is not limited by them.

EXAMPLES

Preparation Example 1

Red Ginseng Hydrolysis Concentrate (1) By adding purified water to a mixture containing bamboo shoot at 38% by weight, Japanese gerbera (*Leibnitzia anandria*) leaf at 16% by weight, oriental arbor vitae (*Platycladus orientalis*) fruit at 30% by weight, and false daisy (*Eclipta prostrata*) at 16% in a ratio of 8 (v/w) with respect to the mixture followed by extraction for 8 hours at 95° C. and filtration, an extract was prepared.

(2) By adding water to *Ecklonia cava* in a ratio of 8 (v/w) with respect to *Ecklonia cava* followed by extraction for 8 hours at 95° C., an *Ecklonia cava* extract was prepared.

(3) By adding the extract prepared in the above step (1) to 6-year-old red ginseng in a ratio of 10 (v/w) with respect to the red ginseng followed by first extraction for 8 hours at 85° C. and filtration, a first red ginseng extract was prepared. By adding the extract prepared in the above step (1) to red ginseng, which has been separated from the first red ginseng extract as prepared in the above, in a ratio of 5 (v/w) with respect to the red ginseng followed by second extraction for 8 hours at 85° C. and filtration, a second red ginseng extract was prepared. By adding the extract prepared in the above step (1) to red ginseng, which has been separated from the second red ginseng extract as prepared in the above, in a ratio of 5 (v/w) with respect to the red ginseng followed by third extraction for 8 hours at 85° C. and filtration, a third red ginseng extract was prepared.

(4) By adding the *Ecklonia cava* extract prepared in the above step (2) to red ginseng, which has been separated from the third red ginseng extract prepared in the above step (3), in a ratio of 5 (v/w) with respect to the red ginseng followed by fourth extraction for 8 hours at 85° C. and filtration, a fourth red ginseng extract was prepared. By adding the *Ecklonia cava* extract prepared in the above step (2) to red ginseng, which has been separated from the fourth red ginseng extract prepared above, in a ratio of 5 (v/w) with respect to the red ginseng followed by fifth extraction for 8 hours at 85° C. and filtration, a fifth red ginseng extract was prepared.

(5) By mixing the first red ginseng extract, the second red ginseng extract, and the third red ginseng extract prepared in the above step (3) with the fourth red ginseng extract and the fifth red ginseng extract prepared in the above step (4) followed by centrifugation at 10° C. or lower and concentration under reduced pressure, red ginseng concentrate (moisture content of not more than 36%) was prepared.

(6) By adding the red ginseng concentrate prepared in the above step (5) to an enzyme solution in which enzymes (beta-glucosidase and pectinase were admixed with each other) are mixed in purified water, which has been sterilized for 30 minutes at 90° C., a red ginseng diluent with Brix value of 5 to 10 was prepared.

(7) By adding 70 to 80% (v/v) alcohol to a red ginseng reaction solution in which the red ginseng diluent prepared in the above step (6) has been subjected to an enzyme reaction for 4 days at 50° C., a mixture solution of red ginseng and alcohol was prepared.

(8) After centrifuging the mixture solution of red ginseng and alcohol prepared in the above step (7) at 5,000 to 80,000 rpm, the supernatant separated by centrifuge was concentrated under reduced pressure till to have Brix value of 60 to 75.

Comparative Example 1

Red Ginseng Hydrolysis Concentrate (1) By adding purified water to 6-year-old red ginseng in a ratio of 10 (v/w) with respect to the red ginseng followed by first extraction for 8 hours at 85° C. and filtration, a first red ginseng extract was prepared. By adding purified water to red ginseng, which has been separated from the first red ginseng extract prepared above, in a ratio of 5 (v/w) with respect to the red ginseng followed by second extraction for 8 hours at 85° C. and filtration, a second red ginseng extract was prepared. By adding purified water to red ginseng, which has been separated from the second red ginseng extract prepared above, in a ratio of 5 (v/w) with respect to the red ginseng followed by third extraction for 8 hours at 85° C. and filtration, a third red ginseng extract was prepared. By adding purified water to red ginseng, which has been separated from the third red ginseng extract prepared above, in a ratio of 5 (v/w) with respect to the red ginseng followed by fourth extraction for 8 hours at 85° C. and filtration, a fourth red ginseng extract was prepared. By adding purified water to the red ginseng, which has been separated from the fourth red ginseng extract prepared above, in a ratio of 5 (v/w) with respect to the red ginseng followed by fifth extraction for 8 hours at 85° C. and filtration, a fifth red ginseng extract was prepared.

(2) By mixing the first red ginseng extract, the second red ginseng extract, the third red ginseng extract, the fourth red ginseng extract, and the fifth red ginseng extract prepared in the above step (1) followed by centrifugation at 10° C. or lower and concentration under reduced pressure, red ginseng concentrate (moisture content of not more than 36%) was prepared.

(3) By adding the red ginseng concentrate prepared in the above step (2) to an enzyme solution in which enzymes (beta-glucosidase and pectinase were admixed with each other) are mixed in purified water, which has been sterilized for 30 minutes at 90° C., a red ginseng diluent with Brix value of 5 to 10 was prepared.

(4) By adding 70 to 80% (v/v) alcohol to a red ginseng reaction solution in which the red ginseng diluent prepared in the above step (3) has been subjected to an enzyme reaction for 4 days at 50° C., a mixture solution of red ginseng and alcohol was prepared.

(5) After centrifuging the mixture solution of red ginseng and alcohol prepared in the above step (4) at 5,000 to 80,000 rpm, the supernatant separated by centrifuge was concentrated under reduced pressure till to have Brix value of 60 to 75.

Comparative Example 2

Red Ginseng Hydrolysis Concentrate (1) By adding purified water to a mixture containing bamboo shoot at 38% by weight, Japanese gerbera (*Leibnitzia anandria*) leaf at 16% by weight, oriental arbor vitae (*Platycladus orientalis*) fruit at 30% by weight, and false daisy (*Eclipta prostrata*) at 16% by weight in a ratio of 8 (v/w) with respect to the mixture followed by extraction for 8 hours at 95° C. and filtration, an extract was prepared.

(2) By adding the extract prepared in the above step (1) to 6-year-old red ginseng in a ratio of 10 (v/w) with respect to the red ginseng followed by first extraction for 8 hours at 85° C. and filtration, a first red ginseng extract was prepared. By adding the extract prepared in the above step (1) to red ginseng, which has been separated from the first red ginseng extract prepared above, in a ratio of 5 (v/w) with respect to the red ginseng followed by second extraction for 8 hours at 85° C. and filtration, a second red ginseng extract was prepared. By adding the extract prepared in the above step (1) to red ginseng, which has been separated from the second red ginseng extract prepared above, in a ratio of 5 (v/w) with respect to the red ginseng followed by third extraction for 8 hours at 85° C. and filtration, a third red ginseng extract was prepared. By adding the extract prepared in the above step (1) to red ginseng, which has been separated from the third red ginseng extract prepared above, in a ratio of 5 (v/w) with respect to the red ginseng followed by fourth extraction for 8 hours at 85° C. and filtration, a fourth red ginseng extract was prepared. By adding the extract prepared in the above step (1) to red ginseng, which has been separated from the fourth red ginseng extract prepared above, in a ratio of 5 (v/w) with respect to the red ginseng followed by fifth extraction for 8 hours at 85° C. and filtration, a fifth red ginseng extract was prepared.

(3) By mixing the first red ginseng extract, the second red ginseng extract, the third red ginseng extract, the fourth red ginseng extract, and the fifth red ginseng extract prepared in the above step (2) followed by centrifugation at 10° C. or lower and concentration under reduced pressure, red ginseng concentrate (moisture content of not more than 36%) was prepared.

(4) By adding the red ginseng concentrate prepared in the above step (3) to an enzyme solution in which enzymes (beta-glucosidase and pectinase were admixed with each other) are mixed in purified water, which has been sterilized for 30 minutes at 90° C., a red ginseng diluent with Brix value of 5 to 10 was prepared.

(5) By adding 70 to 80% (v/v) alcohol to a red ginseng reaction solution in which the red ginseng diluent prepared in the above step (4) has been subjected to an enzyme reaction for 4 days at 50° C., a mixture solution of red ginseng and alcohol was prepared.

(6) After centrifuging the mixture solution of red ginseng and alcohol prepared in the above step (5) at 5,000 to 80,000 rpm, the supernatant separated by centrifuge was concentrated under reduced pressure till to have Brix value of 60 to 75.

Comparative Example 3

Red Ginseng Hydrolysis Concentrate (1) By adding water to *Ecklonia cava* in a ratio of 8 (v/w) with respect to *Ecklonia cava* followed by extraction for 8 hours at 95° C. and filtration, an *Ecklonia cava* extract was prepared.

(2) By adding the *Ecklonia cava* extract prepared in the above step (1) to 6-year-old red ginseng in a ratio of 10 (v/w) with respect to the red ginseng followed by first extraction for 8 hours at 85° C. and filtration, a first red ginseng extract was prepared. By adding the *Ecklonia cava* extract prepared in the above step (1) to red ginseng, which has been separated from the first red ginseng extract prepared above, in a ratio of 5 (v/w) with respect to the red ginseng followed by second extraction for 8 hours at 85° C. and filtration, a second red ginseng extract was prepared. By adding the *Ecklonia cava* extract prepared in the above step (1) to red ginseng, which has been separated from the second red ginseng extract prepared above, in a ratio of 5 (v/w) with respect to the red ginseng followed by third extraction for 8 hours at 85° C. and filtration, a third red ginseng extract was prepared. By adding the *Ecklonia cava* extract prepared in the above step (1) to red ginseng, which has been separated from the third red ginseng extract prepared above, in a ratio of 5 (v/w) with respect to the red ginseng followed by fourth extraction for 8 hours at 85° C. and filtration, a fourth red ginseng extract was prepared. By adding the *Ecklonia cava* extract prepared in the above step (1) to red ginseng, which has been separated from the fourth red ginseng extract prepared above, in a ratio of 5 (v/w) with respect to the red ginseng followed by fifth extraction for 8 hours at 85° C. and filtration, a fifth red ginseng extract was prepared.

(3) By mixing the first red ginseng extract, the second red ginseng extract, the third red ginseng extract, the fourth red ginseng extract, and the fifth red ginseng extract prepared in the above step (2) followed by centrifugation at 10° C. or lower and concentration under reduced pressure, red ginseng concentrate (moisture content of not more than 36%) was prepared.

(4) By adding the red ginseng concentrate prepared in the above step (3) to an enzyme solution in which enzymes (beta-glucosidase and pectinase were admixed with each other) are mixed in purified water, which has been sterilized for 30 minutes at 90° C., a red ginseng diluent with Brix value of 5 to 10 was prepared.

(5) By adding 70 to 80% (v/v) alcohol to a red ginseng reaction solution in which the red ginseng diluent prepared in the above step (4) has been subjected to an enzyme reaction for 4 days at 50° C., a mixture solution of red ginseng and alcohol was prepared.

(6) After centrifuging the mixture solution of red ginseng and alcohol prepared in the above step (5) at 5,000 to 80,000 rpm, the supernatant separated by centrifuge was concentrated under reduced pressure till to have Brix value of 60 to 75.

1. Method for Measuring Ginsenoside Content

Analysis of ginsenoside content was made by HPLC (High Performance Liquid Chromatography) equipped with UVD (Ultra Visible Detector), and the conditions for analysis are as described in the following Table 1. Formula for calculating the content is the same as the following formula.

Ginsenoside content (mg/g)=$S\times(a\times b)$/Collected sample amount (g)

S: Concentration of each ginsenoside in test solution (mg/ml)

a: Total volume of test solution (ml)

b: Dilution fold

TABLE 1

| Conditions for ginsenoside analysis | |
| --- | --- |
| Device | HPLC Agilent 1260 Series |
| Detector | DAD detector (203 nm) |
| Column | Prontosil 120-5-C18-ace-EPS (4.6 mm × 250 mm, 5.0 μm) |
| Column temperature | 40° C. |
| Mobile phase | Acetonitrile: D.W. (gradient) |
| Flow rate | 1.0 ml/min |
| Injection volume | 10 μl |

Example 1

Analysis Result of Compound K Content in Red Ginseng Hydrolysis Concentrate

The results of analyzing the content of compound K (C-K) in red ginseng concentrate and red ginseng hydrolysis concentrate are the same as those described in the following Tables 2 and 3.

TABLE 2

Analysis result of compound K content (mg/g) when enzyme separation was made with 70% alcohol

| | Sample type | Compound K (C-K) |
| --- | --- | --- |
| Preparation example 1 | Red ginseng concentrate of the step (5) | 0.00 |
| | Red ginseng hydrolysis concentrate of the step (8) | 10.19 |
| | Centrifuge precipitate of the step (8) | 0.31 |
| Comparative example 1 | Red ginseng concentrate of the step (2) | 0.00 |
| | Red ginseng hydrolysis concentrate of the step (5) | 6.34 |
| | Centrifuge precipitate of the step (5) | 0.13 |
| Comparative example 2 | Red ginseng concentrate of the step (3) | 0.00 |
| | Red ginseng hydrolysis concentrate of the step (6) | 8.77 |
| | Centrifuge precipitate of the step (6) | 0.22 |
| Comparative example 3 | Red ginseng concentrate of the step (3) | 0.00 |
| | Red ginseng hydrolysis concentrate of the step (6) | 7.16 |
| | Centrifuge precipitate of the step (6) | 0.32 |

As a result, it was found that compound K is contained in the red ginseng hydrolysis concentrate but not in the red ginseng concentrate. In particular, compound K was contained at 10.19 mg/g in the red ginseng hydrolysis concentrate when the enzyme separation has been made with 70% alcohol, and the highest content, i.e., 10.20 mg/g, was obtained when the enzyme separation has been made with 95% alcohol. Thus, there was no significant difference in the compound K content depending on alcohol concentration.

Furthermore, in the precipitate obtained by removing the supernatant that has been separated by centrifuge, compound K was contained in an amount of 0.13 to 0.32 mg/g, showing the loss rate of about 3%.

TABLE 3

Analysis result of compound K content (mg/g) when enzyme separation was made with 95% alcohol

| | Sample type | Compound K (C-K) |
| --- | --- | --- |
| Preparation example 1 | Red ginseng concentrate of the step (5) | 0.00 |
| | Red ginseng hydrolysis concentrate of the step (8) | 10.20 |
| | Centrifuge precipitate of the step (8) | 0.30 |
| Comparative example 1 | Red ginseng concentrate of the step (2) | 0.00 |
| | Red ginseng hydrolysis concentrate of the step (5) | 6.20 |
| | Centrifuge precipitate of the step (5) | 0.20 |
| Comparative example 2 | Red ginseng concentrate of the step (3) | 0.00 |
| | Red ginseng hydrolysis concentrate of the step (6) | 8.70 |
| | Centrifuge precipitate of the step (6) | 0.24 |
| Comparative example 3 | Red ginseng concentrate of the step (3) | 0.00 |
| | Red ginseng hydrolysis concentrate of the step (6) | 7.15 |
| | Centrifuge precipitate of the step (6) | 0.22 |

Example 2

Analysis Result of Ginsenoside Content

Variation of the 15 types of ginsenosides (mg/g) between the red ginseng concentrate and red ginseng hydrolysis concentrate of Preparation example 1 is described in the following Tables 4 and 5.

TABLE 4

Variation of 15 types of ginsenosides (mg/g) between red ginseng concentrate and red ginseng hydrolysis concentrate (enzyme separation was made with 70% alcohol)

| Type | Red ginseng concentrate of the step (5) | Red ginseng hydrolysis concentrate of the step (8) | Centrifuge precipitate of the step (8) |
|---|---|---|---|
| Rg1 | 5.50 | 1.41 | 0.03 |
| Re | 9.32 | 2.32 | 0.05 |
| Rf | 2.34 | 0.19 | 0.00 |
| Rb1 | 19.2 | 1.11 | 0.01 |
| Rg2 | 1.85 | 2.20 | 0.06 |
| Rc | 11.34 | 0.77 | 0.00 |
| Rb2 | 8.52 | 0.57 | 0.00 |
| Rb3 | 1.54 | 0.09 | 0.00 |
| Rd | 4.77 | 1.16 | 0.03 |
| F2 | 0.00 | 1.21 | 0.04 |
| Rg3 | 1.34 | 1.02 | 0.03 |
| Rk1 | 1.03 | 0.54 | 0.02 |
| Rg5 | 1.18 | 0.66 | 0.02 |
| C-K | 0.00 | 10.19 | 0.31 |
| Rh2 | 0.00 | 0.22 | 0.01 |
| Total of 3 types (Rg1 + Rb1 + Rg3) | 26.0 | 3.54 | 0.06 |
| Total of 15 types | 67.9 | 23.7 | 0.61 |
| Solid content (%) | 70.0 | 60.4 | 88.0 |

As a result, it was found that most of the ginsenosides are reduced according to enzyme treatment of the red ginseng concentrate. Meanwhile, among the ginsenosides, Rg2 has slightly increased as a result of the enzyme treatment. In addition, with regard to F2, C-K, and Rh2 which have not been detected from the red ginseng concentrate, they were found to be newly generated as a result of the enzyme treatment of the red ginseng concentrate.

TABLE 5

Variation of 15 types of ginsenosides (mg/g) between red ginseng concentrate and red ginseng hydrolysis concentrate (enzyme separation was made with 95% alcohol)

| Type | Red ginseng concentrate of the step (5) | Red ginseng hydrolysis concentrate of the step (8) | Centrifuge precipitate of the step (8) |
|---|---|---|---|
| Rg1 | 5.50 | 1.42 | 0.03 |
| Re | 9.32 | 2.34 | 0.06 |
| Rf | 2.34 | 0.18 | 0.00 |
| Rb1 | 19.20 | 1.12 | 0.01 |
| Rg2 | 1.85 | 2.21 | 0.06 |
| Rc | 11.34 | 0.78 | 0.00 |
| Rb2 | 8.52 | 0.59 | 0.00 |
| Rb3 | 1.54 | 0.08 | 0.00 |
| Rd | 4.77 | 1.17 | 0.03 |
| F2 | 0.00 | 1.21 | 0.04 |
| Rg3 | 1.34 | 1.02 | 0.02 |
| Rk1 | 1.03 | 0.53 | 0.03 |
| Rg5 | 1.16 | 0.63 | 0.02 |
| C-K | 0.00 | 10.2 | 0.30 |
| Rh2 | 0.00 | 0.22 | 0.01 |
| Total of 3 types (Rg1 + Rb1 + Rg3) | 26.0 | 3.56 | 0.05 |
| Total of 15 types | 67.9 | 23.7 | 0.61 |
| Solid content (%) | 70.0 | 60.5 | 87.9 |

Example 3

Sensory Test of Red Ginseng Concentrate and Red Ginseng Hydrolysis Concentrate

Preference evaluation of the red ginseng concentrate and red ginseng hydrolysis concentrate of Preparation example 1 was performed by evaluating, based on 5-point scale method, the taste, bitterness, appearance, and overall preference, and obtaining their mean value. For the preference for bitterness, higher score is given to less bitterness.

TABLE 6

Sensory Test

| | Sample | |
|---|---|---|
| Evaluation item | Red ginseng concentrate of the step (5) | Red ginseng hydrolysis concentrate of the step (8) |
| Taste | 3.4 | 4.0 |
| Bitterness | 3.8 | 4.2 |
| Appearance | 4.0 | 3.9 |
| Overall preference | 3.6 | 4.1 |

As a result, it was found that the bitterness is reduced more and higher score is shown, in terms of the taste and overall preference, in the red ginseng hydrolysis concentrate compared to the red ginseng concentrate.

What is claimed is:

1. A method for production of a red ginseng hydrolysis concentrate, the method comprising:
    (1) adding water or alcohol to a mixture containing bamboo shoot, Japanese gerbera (*Leibnitzia anandria*) leaf, oriental arbor vitae (*Platycladus orientalis*) fruit, and false daisy (*Eclipta prostrata*) followed by extraction and filtration to prepare an extract;
    (2) adding water or alcohol to *Ecklonia cava* followed by extraction to prepare an *Ecklonia cava* extract;
    (3) adding the extract prepared in the step (1) to red ginseng followed by extraction and filtration to prepare a red ginseng extract;
    (4) adding the *Ecklonia cava* extract prepared in the step (2) to red ginseng separated from the red ginseng extract prepared in the step (3) followed by extraction and filtration to prepare a red ginseng extract;
    (5) mixing the red ginseng extract prepared in the step (3) with the red ginseng extract prepared in the step (4) followed by concentration to prepare a red ginseng concentrate;
    (6) adding an enzyme solution to the red ginseng concentrate prepared in the step (5) to have an enzyme reaction followed by addition of alcohol to prepare a mixture solution of red ginseng and alcohol; and
    (7) centrifuging the mixture solution of red ginseng and alcohol prepared in the step (6) followed by concentration under reduced pressure of a supernatant separated by the centrifuge.

2. The method of claim 1, wherein the mixture of the step (1) is a mixture containing bamboo shoot at 36 to 40% by weight, Japanese gerbera (*Leibnitzia anandria*) leaf at 14 to 18% by weight, oriental arbor vitae (*Platycladus orientalis*) fruit at 28 to 32% by weight, and false daisy (*Eclipta prostrata*) at 14 to 18% by weight based on the total weight of the mixture.

3. The method of claim 1, wherein the step (2) comprises: adding the water or the alcohol to the *Ecklonia cava* in a ratio of 7 to 9 (v/w) with respect to the *Ecklonia cava* followed by the extraction for 7 to 9 hours at 90° C. to 100° C. to prepare an *Ecklonia cava* extract.

4. The method of claim 1, wherein the enzyme reaction in the step (6) is performed for 3 to 6 days at 45° C. to 65° C.

5. The method of claim 2, wherein the method comprises:
(1) adding the water or the alcohol to the mixture containing, based on the total weight of the mixture, the bamboo shoot at 36 to 40% by weight, the Japanese gerbera (*Leibnitzia anandria*) leaf at 14 to 18% by weight, the oriental arbor vitae (*Platycladus orientalis*) fruit at 28 to 32% by weight, and the false daisy (*Eclipta prostrata*) at 14 to 18% by weight followed by the extraction for 6 to 10 hours at 90° C. to 100° C. and filtration to prepare the extract;
(2) adding the water or the alcohol to the *Ecklonia cava* followed by the extraction for 7 to 9 hours at 90° C. to 100° C. to prepare the *Ecklonia cava* extract;
(3) adding the extract prepared in the step (1) to the red ginseng followed by the extraction and the filtration to prepare the red ginseng extract;
(4) adding the *Ecklonia cava* extract prepared in the step (2) to the red ginseng separated from the red ginseng extract prepared in the step (3) followed by the extraction and the filtration to prepare the red ginseng extract;
(5) mixing the red ginseng extract prepared in the step (3) with the red ginseng extract prepared in the step (4) followed by the concentration to prepare the red ginseng concentrate;
(6) adding the enzyme solution to the red ginseng concentrate prepared in the step (5) to have the enzyme reaction for 3 to 6 days at 45° C. to 65° C. followed by the addition of the alcohol to prepare the mixture solution of red ginseng and alcohol; and
(7) centrifuging the mixture solution of red ginseng and alcohol prepared in the step (6) followed by the concentration under reduced pressure of a supernatant separated by the centrifuge.

6. The method of claim 5, wherein the method comprises:
(1) adding the water or the alcohol to the mixture containing, based on the total weight of the mixture, the bamboo shoot at 36 to 40% by weight, the Japanese gerbera (*Leibnitzia anandria*) leaf at 14 to 18% by weight, the oriental arbor vitae (*Platycladus orientalis*) fruit at 28 to 32% by weight, and the false daisy (*Eclipta prostrata*) at 14 to 18% by weight in a ratio of 7 to 9 (v/w) with respect to the mixture followed by the extraction for 6 to 10 hours at 90° C. to 100° C. and the filtration to prepare the extract;
(2) adding the water or the alcohol to *Ecklonia cava* in the ratio of 7 to 9 (v/w) with respect to *Ecklonia cava* followed by extraction for 7 to 9 hours at 90° C. to 100° C. to prepare the *Ecklonia cava* extract;
(3) adding the extract prepared in the step (1) to the red ginseng followed by the extraction at 80° C. to 90° C. and the filtration to prepare the red ginseng extract;
(4) adding the *Ecklonia cava* extract prepared in the step (2) to the red ginseng separated from the red ginseng extract prepared in the step (3) followed by the extraction at 80° C. to 90° C. and the filtration to prepare the red ginseng extract;
(5) mixing the red ginseng extract prepared in the step (3) with the red ginseng extract prepared in the step (4) followed by the concentration to prepare the red ginseng concentrate;
(6) adding the enzyme solution to the red ginseng concentrate prepared in the step (5) to have the enzyme reaction for 3 to 6 days at 45° C. to 65° C. followed by the addition of 65 to 95% (v/v) alcohol to prepare the mixture solution of red ginseng and alcohol; and
(7) centrifuging the mixture solution of red ginseng and alcohol prepared in the step (6) followed by the concentration under reduced pressure of a supernatant separated by the centrifuge.

* * * * *